United States Patent
Johnston

(10) Patent No.: US 10,492,916 B2
(45) Date of Patent: Dec. 3, 2019

(54) ORTHOPAEDIC SHOULDER IMPLANT

(71) Applicant: David Gerald Johnston, Nova Scotia (CA)

(72) Inventor: David Gerald Johnston, Nova Scotia (CA)

(*) Notice: Subject to any disclaimer, the term of this patent is extended or adjusted under 35 U.S.C. 154(b) by 9 days.

(21) Appl. No.: 15/560,849

(22) PCT Filed: Mar. 23, 2016

(86) PCT No.: PCT/CA2016/000079
§ 371 (c)(1),
(2) Date: Sep. 22, 2017

(87) PCT Pub. No.: WO2016/149792
PCT Pub. Date: Sep. 29, 2016

(65) Prior Publication Data
US 2018/0256348 A1 Sep. 13, 2018

Related U.S. Application Data

(60) Provisional application No. 62/136,915, filed on Mar. 23, 2015.

(51) Int. Cl.
*A61F 2/40* (2006.01)
*A61F 2/30* (2006.01)

(52) U.S. Cl.
CPC .......... *A61F 2/40* (2013.01); *A61F 2002/305* (2013.01); *A61F 2002/30387* (2013.01);
(Continued)

(58) Field of Classification Search
CPC ............... A61F 2/40; A61F 2002/4088; A61F 2002/4092; A61F 2002/4096; A61F 2002/30433; A61F 2002/30578
See application file for complete search history.

(56) References Cited

U.S. PATENT DOCUMENTS 3,979,778 A 9/1976 Stroot et al.
5,108,440 A 4/1992 Grundei et al.
(Continued)

FOREIGN PATENT DOCUMENTS

DE 10164328 A1 7/2003
FR 2418644 A1 9/1979
(Continued)

OTHER PUBLICATIONS

Arntz et al., "Prosthetic Replacement of the Shoulder for the Treatment of Defects in the Rotator Cuff and the Surface of the Glenohumeral Joint," The Journal of Bone and Joint Surgery, Apr. 1993, vol. 75 (4), Abstract only, 1 page.
(Continued)

*Primary Examiner* — Brian A Dukert
(74) *Attorney, Agent, or Firm* — Greenberg Traurig, LLP

(57) ABSTRACT

A shoulder implant for reestablishing a coracoacromial arch in a subject, the shoulder implant comprising: a dorsal surface substantially shaped as a coracoacromial arch of a shoulder, the dorsal surface for engaging at least a posterior portion of the acromium of the subject when implanted in the subject; and an inferior surface substantially shaped as an acromiohumeral arch of a shoulder, the dorsal surface being opposite the inferior surface. The implant may have a spacer having a convex shape to simulate the anatomic contour of a acromiohumeral arch and the spacer coupled to a baseplate. In certain embodiments, the baseplate and the spacer have a convex surface that may extend the length of the inferior surface of the acromium and anteriorly to the coracoid process.

20 Claims, 13 Drawing Sheets

(52) U.S. Cl.
CPC ............... *A61F 2002/30433* (2013.01); *A61F 2002/30578* (2013.01); *A61F 2002/4088* (2013.01); *A61F 2002/4096* (2013.01)

(56) References Cited

U.S. PATENT DOCUMENTS

| | | | |
|---|---|---|---|
| 5,944,757 | A | 8/1999 | Grammont |
| 6,989,032 | B2 | 1/2006 | Errico et al. |
| 7,517,364 | B2 | 4/2009 | Long et al. |
| 7,585,327 | B2 | 9/2009 | Winslow et al. |
| 7,799,077 | B2 | 9/2010 | Lang et al. |
| 7,959,680 | B2 * | 6/2011 | Stone .................... A61F 2/4081 623/19.11 |
| 8,231,684 | B2 | 7/2012 | Mutchler et al. |
| 8,709,089 | B2 | 4/2014 | Lang et al. |
| 2006/0079963 | A1 | 4/2006 | Hansen et al. |
| 2006/0195194 | A1 | 8/2006 | Gunther et al. |
| 2007/0244563 | A1 | 10/2007 | Roche et al. |
| 2014/0371864 | A1 | 12/2014 | Shohat et al. |

FOREIGN PATENT DOCUMENTS

| | | |
|---|---|---|
| FR | 2541890 A1 | 9/1984 |
| WO | 2004032806 A1 | 4/2004 |
| WO | 2009/023250 A1 | 2/2009 |
| WO | 2010/127854 A2 | 11/2010 |
| WO | 2014/153557 A2 | 9/2014 |

OTHER PUBLICATIONS

International Patent Application No. PCT/CA2016/000079, International Preliminary Report on Patentability dated Oct. 5, 2017.

Petroff et al., "Bipolar Shoulder Arthroplasty for Irreparable Rotator Cuff Tear: A Preliminary Report and a Video Fluoroscopy Study," RCO, 1999, vol. 85, pp. 245-256.

International Search Report and Written Opinion dated Jun. 8, 2016, issued by the Canadian Intellectual Property Office in International Application No. PCT/CA2016/000079 (7 pages).

* cited by examiner

A

B

C

D

A

B

A

B

C

ORTHOPAEDIC SHOULDER IMPLANT

CROSS REFERENCE TO RELATED APPLICATIONS

This application claims the benefit of priority of U.S. Provisional Patent Application No. 62/136,915 filed Mar. 23, 2015, which is hereby incorporated by reference.

FIELD

The present disclosure relates to orthopaedic shoulder implants. The orthopaedic implants disclosed herein are subacromial implants shaped to simulate the contour of a naturally occurring coracoacromial arch.

BACKGROUND

Rotator cuff disease is prevalent in the general population and is a significant cause of shoulder pain and dysfunction in the orthopaedic patient. A large to massive tear of the rotator cuff can lead to chronic pain and loss of function (i.e. motion and strength) through the shoulder. Loss of the normal integrity of the rotator cuff as a result of a massive cuff tear can lead to superior migration of the humeral head and uncoupling of the humeral head with the adjacent glenoid. This uncoupling or incongruency of the glenohumeral (shoulder) joint can cause pain and loss of function. This is a particularly difficult problem in the active person in his/her middle years who may still be working or involved in leisure activities that have a physical demand on the impaired shoulder.

In the older patient, a longstanding massive cuff tear can lead to a secondary osteoarthritis of the shoulder joint referred to as 'cuff tear arthropathy'. In the sedentary elderly patient with cuff tear arthropathy, a particular type of shoulder replacement, 'reverse' shoulder prosthesis can be used to relieve severe pain and restore shoulder function. The reverse shoulder replacement is a complex implant that requires insertion of glenoid and humeral components. However, in the younger, physically active patient, it is desirable to minimize or delay the onset of cuff tear arthropathy. In addition, reverse shoulder replacement in the younger, physically active person may lead to premature failure of the implant and therefore may not be a prudent surgical choice.

Large to massive rotator cuff tears present a surgical challenge and it may not be possible to achieve a competent repair when there is a lack of residual tendon (cuff), poor quality of remaining tendon or inelasticity (immobility) of the muscle/tendon unit. These large tears that cannot be repaired, or that recur after initial repair, present a significant treatment challenge. Some surgical solutions have included various 'patches' to cover the defect, tendon transfers (eg. latissimus dorsi) and prosthetic shoulder replacements. These surgeries can be complex with less than optimum outcomes.

A number of implants have been described which reduce 'superior' migration of the humeral head in the patient with a rotator cuff tear. U.S. Pat. No. 6,712,854 B2 and US Patent Application No. 2007/0078477A1 disclose spacers that are adfixed to the overlying acromium and are designed to prevent superior migration. However these implants are adfixed to the relatively thin acromium which could lead to inadequate initial fixation, premature loosening of the implant, or catastrophic fracture and or bone loss of the acromium.

US. Patent Application No. 2011/0178603 A1 discloses an orthopaedic shoulder implant that is configured to be positioned at the midpoint of the glenoid above the superior surface of the glenoid. Stable fixation of the implant requires placement of a bore hole and insertion of a pin (screw) through the superior surface of the glenoid and into the base of the coracoid. Loosening of this implant or later removal of a well fixed implant with associated cement can lead to glenoid bone loss and substantially compromise stable insertion of a future glenoid prosthesis which is required with a reverse shoulder replacement or other type of 'total' shoulder replacement. In addition, this acromial spacer is composed solely of a polymer (e.g. high density polyethylene) and would not allow for biologic fixation of the implant to host bone of the scapula.

It is an object of the present disclosure to obviate or mitigate at least one disadvantage of previous shoulder implants.

SUMMARY

Disclosed herein is an orthopaedic shoulder implant that re-establishes the shape and integrity of the coracoacromial arch. In some embodiments, the implant maintains the normal dimensions of the subacromial space (acromiohumeral height). The implant reduces or prevents superior (to also mean, posterosuperior or anterosuperior) displacement of the humeral head. Advantageously, embodiments of the disclosed implant allow for stable biologic fixation without compromise of the glenoid or acromium.

Disclosed herein is a shoulder implant for reestablishing a coracoacromial arch in a subject, the shoulder implant comprising a body, the body comprising a dorsal surface substantially shaped as a coracoacromial arch of a reference shoulder, the dorsal surface for engaging at least a posterior portion of the acromium of the subject when implanted in the subject; and an inferior surface substantially shaped as an acromiohumeral arch of a shoulder, the dorsal surface being opposite the inferior surface. The subject may be a human.

The dorsal surface may be sized and shaped to coextensive with an acromium inferior surface of the acromium of the subject. In an embodiment, the shoulder implant has a thickness that allows the restoration of the acromiohumeral height of the shoulder of the subject to the acromiohumeral height of a control shoulder, when implanted in the subject. In an embodiment, the shoulder implant is of a thickness that maintains the acromiohumeral height of the shoulder of the subject as compared to a control shoulder, when implanted in the subject. The control shoulder may be an uninjured shoulder of the subject or an average of a population representative of the subject.

The shoulder implant may have a spacer having a convex shape to simulate the anatomic contour of a acromiohumeral arch, the spacer being coupled to a baseplate. In certain embodiments, the baseplate and the spacer have a convex surface that may extend the length of the inferior surface of the acromium and anteriorly to the coracoid process.

The shoulder implant may comprise a spacer, the spacer comprising the inferior surface and comprising a second surface opposite the inferior surface. The shoulder implant may further comprise a baseplate comprising the dorsal surface and comprising a second surface opposite the dorsal surface; the second surface of the spacer being coupled to the second surface of the baseplate. The spacer may extend the length of the baseplate. The spacer may comprise at least one coupling feature and the baseplate may comprise at least one complementary coupling feature for engaging with the at least one coupling feature on the spacer for coupling the baseplate to the spacer. The at least one coupling feature of the spacer is a female dove-tail snap-fit element and the at least one complementary coupling feature of the baseplate is a male dove-tail snap-fit element. Alternatively, the at least one coupling feature of the spacer may a threaded anchor and the at least one complementary coupling feature of the baseplate may be a recess defined by the anterior surface of the baseplate, the recess having complementary threads for receiving the threaded anchor and for securing together the baseplate and spacer.

The baseplate may define at least one aperture to receive a respective mounting member, each mounting member for coupling the shoulder implant to a native or prosthetic bone of the subject. The baseplate comprises a baseplate anterior portion and a baseplate posterior portion and in an embodiment the at least one aperture is defined in the baseplate posterior portion for receiving a respective mounting member and for coupling the shoulder implant to a dorsum of a spinous process of the subject.

In an embodiment, the baseplate defines two apertures, one of which is defined in the baseplate anterior portion for receiving a respective mounting member for coupling the shoulder implant to a coracoid process of the subject.

In a further embodiment, the at least one aperture comprises two apertures and the first aperture is for coupling the implant to a dorsum of a spinous process of the subject, wherein the baseplate defines a second aperture positioned in the posterior end of the baseplate for receiving a mounting member for coupling the implant to a scapular spine of the subject. The mounting member may be a pin or a screw.

The spacer may be an articulating spacer made of biocompatible polymer or ceramic. In an embodiment, the baseplate is a metal baseplate.

The shoulder implant may further comprise a stabilization member coupled to the body for stabilizing the implant when implanted in the subject. The stabilization member may be positioned at an anterior end of the body or at a posterior end of the body or at both the anterior end and posterior end of the body. The stabilization member may be a scapular spine extension that extends posteriorly from a posterior end of the implant and is shaped to allow fixation to a scapular spine of a subject. The scapular spine extension may comprise a surface that defines one or more apertures each for receiving a mounting member for coupling the implant to the scapular spine of the subject. The stabilization member may be a coracoid extension extending anteriorly from an anterior end of the implant and shaped to engage a coracoid of the subject, for securing the baseplate to the coracoid. The coracoid extension may comprise one or more apertures each for receiving a mounting member for coupling the implant to the coracoid of the subject.

The shoulder implant may further comprise a biological fixation member for allowing bone ingrowth and biological fixation of the implant to the bone. Any or all of the baseplate, or either of the stabilization members may comprise the biological fixation member. The baseplate may comprise a biological fixation member for allowing bone ingrowth and biological fixation of the implant to the bone. The stabilization member may comprise a biological fixation member for allowing bone ingrowth and biological fixation of the implant to the bone. The biological fixation member may be a metallic mesh. The biological fixation member may comprise a hydroxyapatite coating. The biological fixation member may comprise a portion of the shoulder implant dorsal surface which comprises an altered texture relative to a remainder of the shoulder implant dorsal surface.

In an embodiment, the shoulder implant comprises an anterior end portion; a posterior end portion adjacent opposite the anterior end portion; and a coracoacromial arch portion extending between the anterior end portion and the posterior end portion, wherein the coracoacromial arch portion has an arc radius which substantially corresponds to the arch radius of a humerus. The arc radius may be about 20 mm to about 25 mm.

In certain embodiments the implant comprises a spacer coupled to a baseplate having a shape that approximates the anatomic contour of a coracoacromial arch, and a stabilizing member coupled to the baseplate. In certain embodiments, the baseplate is sized and shaped to extend the length and width of the inferior surface of the acromium. In certain embodiments, the spacer may have a surface that extends along a length of the inferior surface of the acromium and simulates the anatomic contour of a coracacromial arch.

In certain embodiments, the spacer is an articulating spacer and extends the length of the baseplate. The baseplate may comprise an altered surface or may comprise a member for allowing bone ingrowth and biological fixation of the baseplate to a bone.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

The present disclosure relates to orthopaedic shoulder implants that may be used for correcting rotator cuff injuries. The orthopaedic implants disclosed herein are shaped to simulate the contour of a naturally occurring coracoacromial arch and may be shaped to restore the space between the inferior surface of the acromium and the humeral head (acromiohumeral height). The implants disclosed herein reduce superior migration of the humeral head and do not compromise the integrity of the glenoid which is an important consideration for future surgery. As used herein, the term "superior" encompasses anterosuperior and posterosuperior migration of the humeral head.

Figure 1:
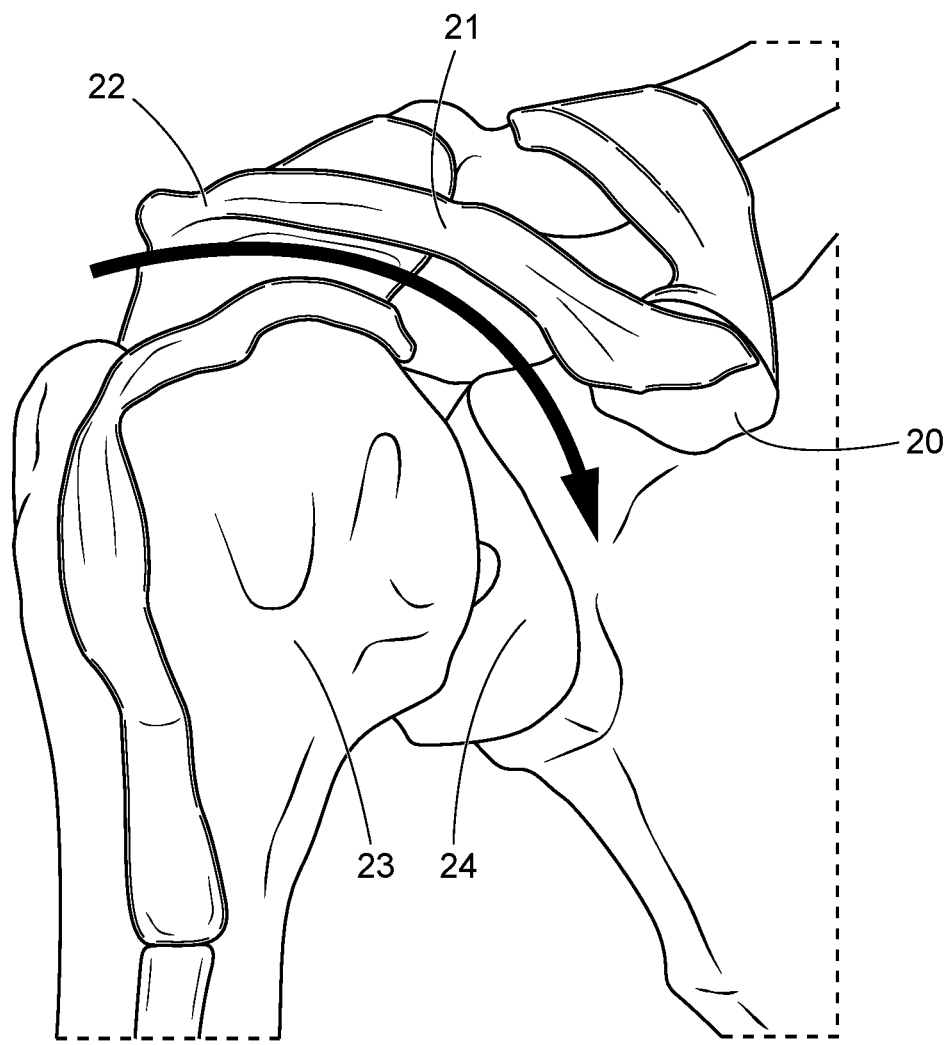
FIG. 1 is a frontal view of a shoulder showing the normal coracoacromial arch.

FIG. 1 is a frontal view view of a normal human shoulder. The coracoacromial arch (CA) of the shoulder (depicted by the arrow) is comprised of an intact coracoid process 20, the CA ligament 21 and the acromium 22. The coracoacromial arch is a protective arch formed by the smooth inferior aspect of the acromium 22 and the coracoid process 20 of the scapula with the coracoacromial ligament 21 spanning between the acromium 22 and the coracoid process 20. The head 23 of the humerus fits into the glenoid 24. An intact coracoacromial arch in conjunction with a competent rotator cuff maintains normal glenohumeral joint anatomy. Superior migration of the humeral head can occur in the patient with a massive cuff tear. The coracoacromial arch can be compromised through the chronic degenerative changes which occur during the natural history of rotator cuff disease or following surgical treatment (surgical acromioplasty and resection of the CA ligament) performed in a rotator cuff patient.

Disclosed herein is a shoulder implant for stabilizing a shoulder in a subject. The shoulder implant comprises a dorsal surface substantially shaped as a coracoacromial arch. By "substantially shaped" it is meant that the dorsal surface of the surface is curved to mimic the CA of a shoulder. It can be appreciated that the size and shape of the curvature of a CA will vary between individuals depending on, for example, their age, height or size. Thus, the term "substantially shaped" includes variations so long as the surface is curved in the general shape of a naturally occurring CA that would be present in a subject. The shoulder implant further comprises an inferior surface substantially shaped as an acromiohumeral arch of the subject. By "substantially shaped as an acromiohumeral arch" it is meant that the surface is generally curved to mimic the contour between the dorsal surface of the humeral head and the overlying CA arch. The degree of curvature and the size of the acromiohumeral arch will vary from subject to subject. Therefore the term "substantially shaped" it is meant that variations in the shape are acceptable as long as the shape is similar to a naturally occurring acromiohumeral arch. The shoulder implant may have a thickness that restores or increases the height of the subacromial space when implanted in the subject. As described elsewhere, the thickness of the implant will vary depending on the size of the subject and, accordingly the size of the subacromial space.

In an embodiment the shoulder implant comprises an anterior end portion, a posterior end portion opposite the anterior end portion; and a coracoacromial arch portion positioned between the anterior portion and the posterior portion, wherein the coracoacromial arch portion has an arch radius which substantially corresponds to a radius of a humerus, and preferably the humerus of the subject. The term "substantially corresponds" means that the arch radius is similar to the radius of a natural, biological humerus. However, as there is a certain amount of variation between the sizes of humerus in a population of subjects, the term encompasses an amount of variation to reflect the variation of humerus size and shape between subjects.

Figure 2:
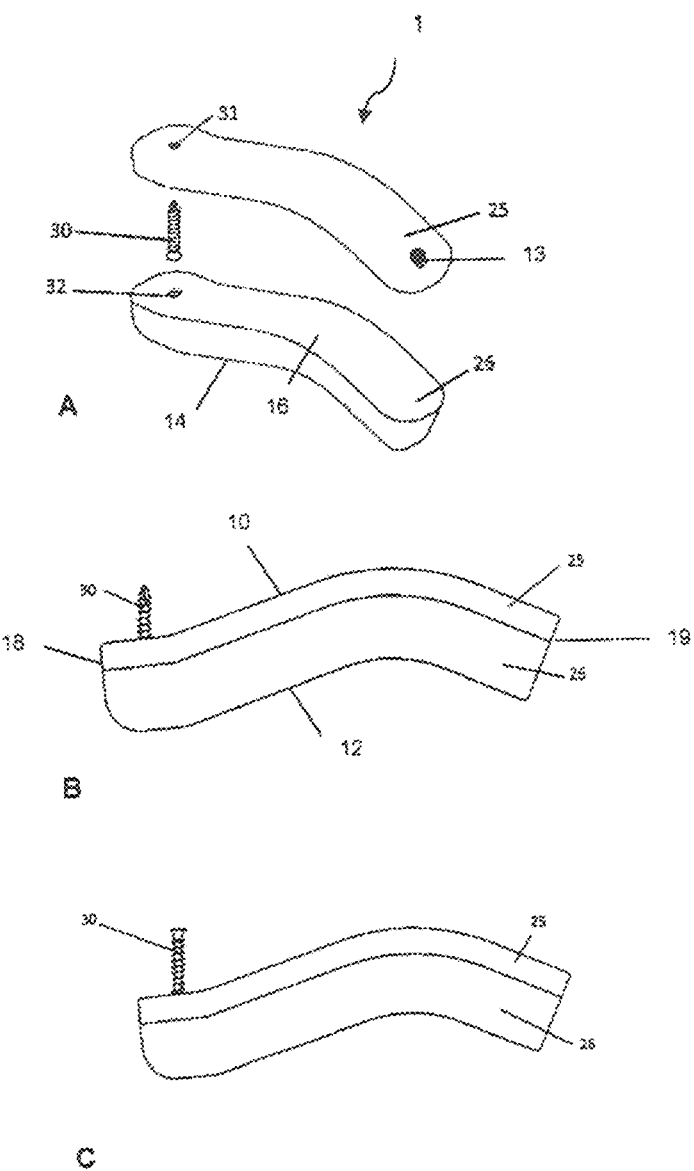
FIG. 2A is an exploded isometric view of a shoulder implant in accordance with one embodiment disclosed herein.
FIG. 2B is a front view of the shoulder implant shown in FIG. 2A wherein a screw travels though the baseplate and into an overlying bone (not shown)
FIG. 2C is a front view of the shoulder implant shown in FIG. 2A wherein a screw travels through an overlying bone (not shown) and into the implant.

FIG. 2A is an exploded view of an embodiment of a shoulder implant 1. A baseplate 25 is coupled to a spacer 26. Baseplate 25 has a dorsal surface (shown generally at 10) which articulates with the acromium and is shaped to reproduce the anatomic contour of the coracoacromial arch. Baseplate 25 comprises a second surface (not shown) opposite the dorsal surface 10 that engages a surface 16 of the spacer 26 when the implant is assembled (as in FIG. 2B and FIG. 2C). At least a portion of a posterior portion of the dorsal surface 10 abuts the overlying acromial surface when inserted into a patient to allow the initial fixation of the implant and to allow biological ingrowth of the bone. The dorsal surface 10 of the baseplate 25 may contact the entirety of the overlying acromial surface when inserted into a patient. In some embodiments the dorsal surface 10 of the baseplate 25 extends the length and width of the inferior surface of the acromium thereby providing full coverage of the acromium. The inferior surface of the implant articulates against the humeral head. The baseplate 25 defines an aperture 13 on a posterior end portion of a posterior end 19 of the implant for receiving a mounting member (not shown) and coupling the implant through the dorsum of the scapular spine of the subject to the posterior acromium. The spacer 26 has an inferior surface (not shown) positioned opposite surface 16, Inferior surface is substantially shaped as an acromiohumeral arch of a shoulder (element 12 shows a side view of the profile of the inferior surface). In the embodiment shown in FIGS. 2A, 2B and 2C, the baseplate 25 is sized to extend to the coracoid process and has a second, optional, aperture 31 (or borehole) for receiving a mounting member 30 at the tip of the anterior limb to allow stabilization of the baseplate 25 to the coracoid process 20. In this embodiment, the mounting member 30 is an orthopaedic screw, however any other means known in the art for securing an implant to a native bone or prosthetic bone may be used. For example, the mounting member may be a pin. Spacer 26 comprises a recess 32 shaped to receive the head of the mounting member 30.

Figure 10:
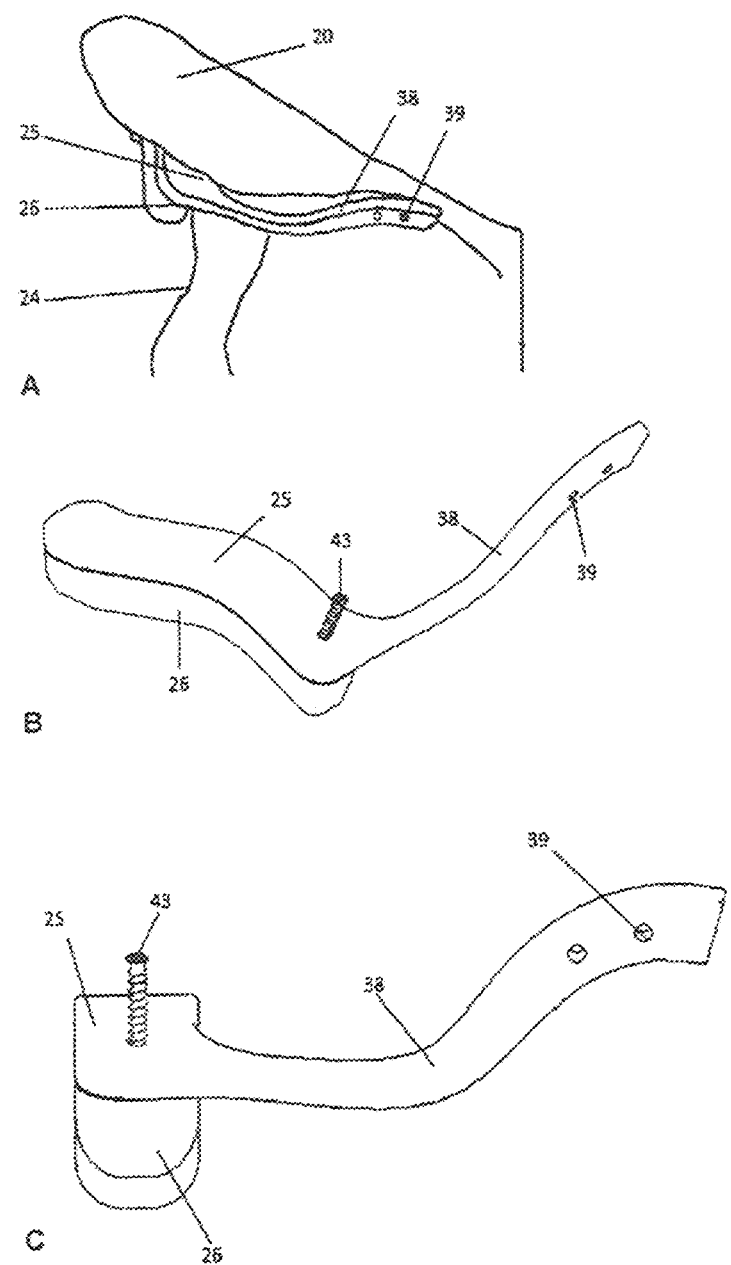
FIG. 10A is an exploded front view of an embodiment of an implant in accordance with the present disclosure having a posterior stabilizing member extending from a posterior end of the implant that may be secured to the scapular spine of the subject and showing the positioning of the implant in a shoulder.
FIG. 10B is an isometric view of the embodiment of the implant shown in FIG. 10A.
FIG. 10C is a right view of the embodiment of the implant shown in FIG. 10A showing posterior/acromium screw fixation points.

FIGS. 2B and 2C depict the general placement and direction of mounting member 30 for fixing the shoulder implant to the coracoid process (not shown). Stable fixation of the shoulder implant to the acromium may be achieved with a mounting member, such as an orthopaedic screw or pin placed through an anterior portion at an anterior end 18 of the implant and into the coracoid process (not shown) (FIG. 2B) or through the bone (not shown) and into the baseplate (FIG. 2C). In accordance with the embodiment shown, the screw can be inserted in a different place and or direction on the coracoid for fixation of the anterior limb to the baseplate. Although FIGS. 2A-2C depicts the positioning of an anterior mounting member it is understood that the mounting member securing the posterior end of the implant may be inserted through the dorsum of the scapula spine to secure the implant to the posterior acromium (as described further in the embodiment shown in FIG. 10). Alternatively, it is possible to place one or more additional screws through the implant and into the posterior acromium. At least one point of posterior fixation is preferable in order to secure the implant within the shoulder of the subject. The mounting member, for example, an orthopedic screw or pin, can optionally be coated, for example, with hydroxyapatite or a similar material that promotes bone growth to allow for biologic fixation to a host bone.

The baseplate can be manufactured from, but not limited to, any of the commonly used orthopaedic metals or alloys, such as titanium, cobalt, chromium, molybdenum, or stainless steel. The baseplate may be manufactured in various sizes to allow for the variation in size of anatomy in the patient population. The baseplate may be made of various thicknesses and its dimensions of width and length may approximate but are not limited to the anatomic dimensions of the acromium.

The spacer 26 can be manufactured from, but not limited to, a biocompatible polymer or any of the commonly used orthopaedic materials such as ceramic, metals or alloys, such as titanium, cobalt, chromium, molybdenum, or stainless steel. In certain embodiments, the spacer is an articulating spacer. By articulating, it is meant that the spacer allows for movement between the spacer and the underlying native or prosthetic humeral head. The spacer would maintain the normal anatomic relationship of the humeral head to the glenoid and, in part, function to replace the absent rotator cuff and prevent superior migration of the humeral head. Thus, the spacer "articulates" with the underlying humeral head to allow for motion and maintain the normal relationship of the humeral head with the glenoid. The articulating surface can be manufactured in different thicknesses and also can be manufactured in different 'diameters' to match the diameter or contour of the humeral head. The articulating spacer can be manufactured from but not limited to, the common 'bearing materials' used in orthopaedic implants, such as high density polyurethane, ultra high molecular weight polyurethane, ceramic or metal. The spacer can cover the complete surface of the baseplate or be modified to cover only a certain portion of the baseplate. For example, the spacer can extend beyond the baseplate. The spacer is not limited to the shape and dimensions of the baseplate. The spacer should at least mimic the curvature of the acromiohumeral arch. In some embodiments the spacer is not coextensive with the entire width of the baseplate. In some embodiments the width of the spacer is less than the width of either the acromiohumeral or the coracoacromial arch.

In the embodiment shown in FIGS. 2A-2C, the shoulder implant is 'modular' in design. By modular it is meant that the baseplate 25 and the spacer 26 are manufactured separately and assembled either prior to surgery or during surgery. The coupling of the baseplate 25 and spacer 26 is described in detail elsewhere. In other embodiments, the spacer 26 may be designed for permanent attachment to the baseplate 25. In even further embodiments, the shoulder implant can be manufactured as a 'unimodular' or integral implant (baseplate and articulating spacer manufactured as a single unit) of various sizes. In certain embodiments, the implant may be wholly comprised of metal or metal alloy commonly used in orthopaedic implants.

The baseplate may be manufactured in various sizes to allow for the variation in size of anatomy in the patient population. The implant sizes are based on known measurements with respect to shoulder joints in the general population. These measurements would be readily accessible to a person of skill in the art. Table 1 summarizes anatomical measurements from known populations that are taken into consideration when sizing an implant or designing an implant.

TABLE 1

Average Measurements of the Anatomy of a Shoulder Joint.

|  | Men | Women |
|---|---|---|
| Acromion Measurements (avg.) | | |
| Length | 48.5 mm | 40.6 mm |
| Anterior Width | 19.5 mm | 18.4 mm |
| Anterior Thickness | 7.7 mm | 6.7 mm |
| Coracoacromial Arch Measurements (avg.) | | |
| Ligament Thickness | 1.3 mm (at midpoint) | |
| Ligament Length | 42 mm | |
| Ligament Height | 20 mm | |
| Humeral Head Diameter | 40-58 mm | |
| Origin | Coracoid process | |
| Insertion | Anterior acromion | |
| Typical Pressure | 20 N (at rest) | |
| Other Measurements (avg.) | | |
| Acromion-Coracoid Length (a) | 28.1 mm (21-39 mm) | |
| Acromion-Glenoid Length (b) | 17.7 mm (13-20 mm) | |
| Acromion Inclination (c) | 22.7° (15-34°) | |
| Coracoid to glenoid length (d) | 20 mm (middle) | |
| Coracoid height | 10 mm | |
| Subacromial Space* w/passive arm | Men - 9.7 mm | |
|  | Women - 9.2 mm | |
| Subacromial Space* w/90° abduct, ext. rotation | 4.4 mm | |
| Subacromial Space* w/120° abduct | 3.9 mm | |
| Subacromial Area | 631 mm$^2$ | |

*Defined as the shortest distance from the interior surface of the acromion to the humeral head REFERENCES for Table 1: eORI F Shoulder Anatomy, Acta Orthopaedica Scandinavica—The normal subacromial space in radiographs, Subacromial space width changes during abduction and rotation—a 3-D MR imaging study Graichen et al; Subacromial volume and rotator cuff tears Does an association exist?, Anthony Yi et al; Morphological parameters of the acromion, Paraskevas et al, In-Vivo Measurement Of Subacromial Space Width During Shoulder Elevation Bey et al; Evaluation of the coracoid and coracoacromial arch geometry on Thiel-embalmed cadavers using the three-dimensional MicroScribe digitizer Alobaidy et al.)

The dimensions of an implant may be determined, for example, based on length/width of the acromium, distance to the coracoid, radius of curvature of the humeral head and height of the subacromial space. The measurements include the coracoid inclination angle, the CA arch radius which is determined based on the average humerus radius; and the acromium inclination angle. In some embodiments the inferior surface of the implant matches the radius of curvature of the native or prosthetic humeral head. In some embodiments the diameter may be about 40 mm to about 42 mm, about 44 mm to about 48 mm, about 50 mm to about 52 mm or about 54 mm to about 56 mm. These various sizes would match the typical diameters of a humeral head in the general Orthopaedic population.

Figure 3:
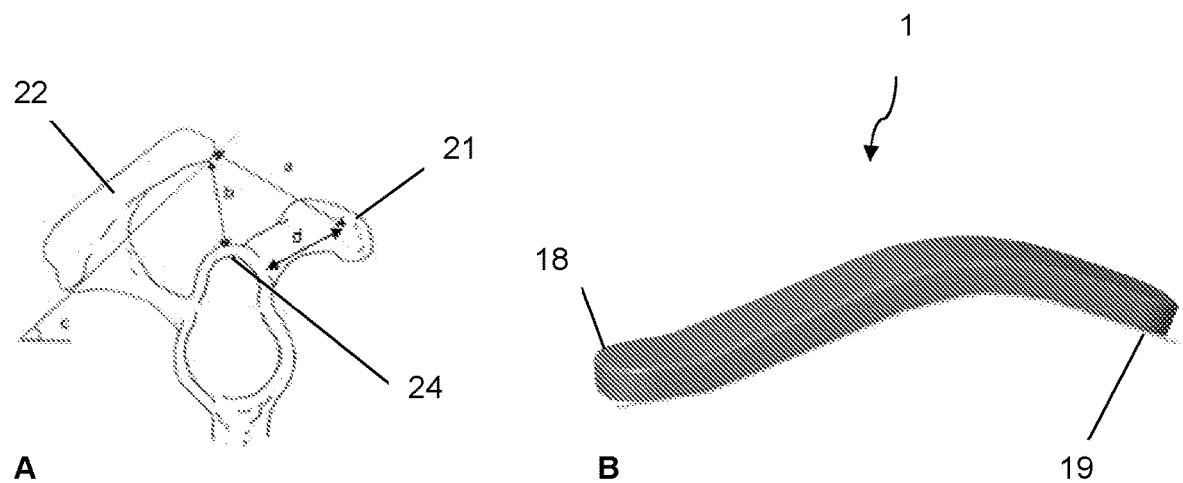
FIG. 3A is a diagram of a shoulder joint showing the calculation of angles and measurements.
FIG. 3B is a diagram of an embodiment of a shoulder implant in accordance with the present disclosure wherein the implant is integrally formed and showing the angles of the inferior surface of the implant.
FIG. 3C shows the angles of a specific embodiment in accordance with the present disclosure of a shoulder implant.
Figure 3:
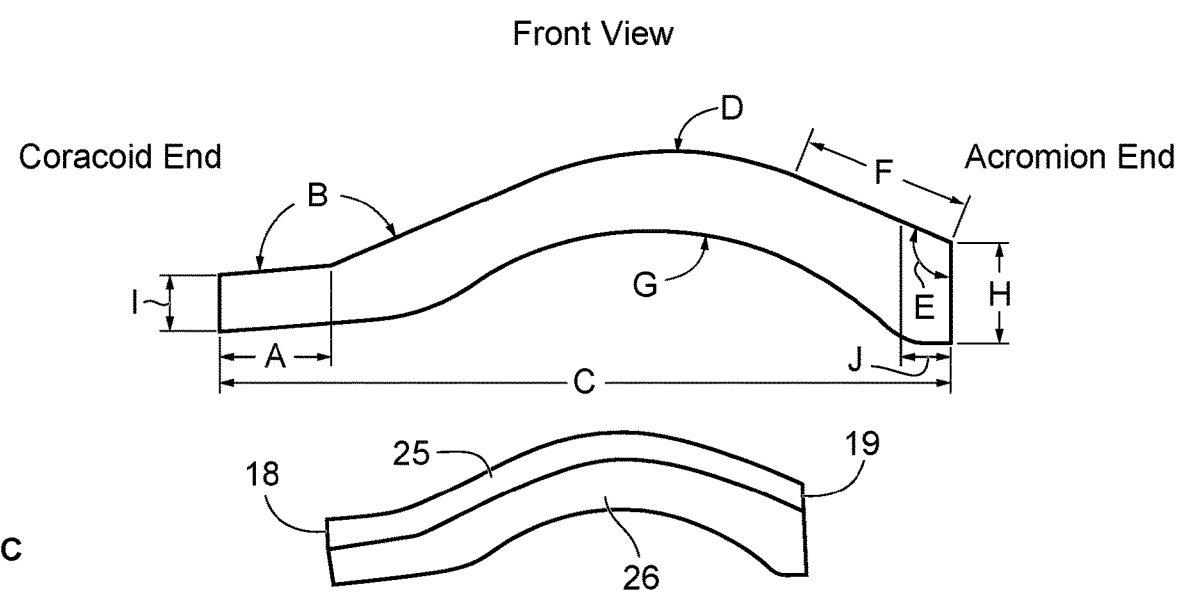

FIG. 3A is a diagram of a shoulder joint showing certain of the measurements and angles outlined in Table 1. The distance between the acromium 22 and the coracoid process 21 (the acromium-coracoid length) is defined by (a). The distance between the acromium 22 and the glenoid 24 (the acromium-glenoid length) is defined by (b). The angle "c" represents the acromium inclination angle. The distance between the coracoid process 21 and the glenoid 24 (the acromium-glenoid length) is shown as (d). FIG. 3B shows an embodiment of the shoulder implant 1 wherein the spacer is integral with the baseplate showing an anterior (or coracoid) end 18 and a posterior (or acromium) end 19.

FIG. 3C (lower portion) shows an embodiment of an implant having a baseplate 25 coupled to a spacer 26. The upper portion of FIG. 3C shows dimensions used to create the curves of dorsal and inferior surface of an embodiment of an implant. In this embodiment, the implant comprises an anterior end portion (A) adjacent the anterior end 18 which serves as an anterior mounting point. (D) defines a coracoacromial arch portion that has an arc radius that generally corresponds to a coracoacromial arch radius of a natural shoulder of a human subject. In this embodiment, the angle (B) of the dorsal surface at the anterior end of the coraacocromial arch portion is determined based on a coracoid inclination angle. A posterior end portion (J) is adjacent the posterior end and opposite the anterior end portion (A) and, in this embodiment, is of a length that corresponds to an average acromium length. Coracoacromial arch portion (D) is positioned between the anterior end portion A and the posterior end portion (J). The shape of the baseplate takes into consideration the acromium inclination angle (E). In some embodiments the length of the implant (C) between the anterior end 18 and the posterior end 19 may be calculated based on the acromium-coracoid length and the acromium length. It will be appreciated that in embodiments comprising a further anterior or posterior stabilizing member the overall length of the implant will be increased accordingly. The inferior surface of the implant in this embodiment is substantially shaped as an acromiohumeral arch of a shoulder and takes into account the radius of the humeral head (G). (H) shows a thickness of the implant at the acromium end and (I) shows a thickness of the implant at the coracoid end. It can be understood that in order to be substantially shaped as a coracoacromial arch it is not required that the baseplate extend to the coracoid as it is possible to maintain the CA arch with a smaller portion of the spacer. In some embodiments the anterior end portion and/or the posterior end portion are not present and the implant has only a curved portion that mimics the coracoacromial arch on the posterior surface and the acromiohumeral arch on the inferior surface.

TABLE 2

Summarizes a range of measurements that are used in some embodiments of the implant.

|  | Feature Description | Typical Sizing |
|---|---|---|
| A | Coracoid length for fixation | 8-10 mm |
| B | Coracoid inclination angle | 130-170° |
| C | Overall length (based on acromion-coracoid length and acromion length) | 50-100 mm |
| D | CA arch radius | 20-25 mm |
| E | Acromium inclination angle | 105-125° |
| F | Acromion length | 15-30 mm |
| G | Humeral head radius | 19-26 mm |
| H | Thickness, acromium end | 5-7 mm |
| I | Thickness, coracoid end | 4-6 mm |

In some embodiments the acromium inclination angle may range from about 105° to about 125°. In some embodiments shows the length of the implant or baseplate is between 50 and 100 mm. In some embodiments the overall length of the implant or baseplate may be about 50 mm to about 68 mm. In some embodiments the overall length of the implant or baseplate is preferably about 53.6 mm, about 60.0 mm, about 61.5 mm, or about 68.5 mm. In some embodiments the coracoid length for fixation is about 8 to about 10 mm. In some embodiments the coracoid inclination angle is between about 130° and about 170°. In some embodiments the thickness of the implant at the acromium end is about 5 mm to about 7 mm. In some embodiments the thickness at a coracoid end is about 4 mm to about 6 mm. In some embodiments, the implant has a thickness that, when implanted in the subject, restores the acromiohumeral height of a shoulder of the subject to substantially the same acromiohumeral height as a control shoulder, wherein the control shoulder is an uninjured shoulder of the subject or an average of a population representative of the subject.

The overall thickness of the implant is important in order as it influences the height of the subacromial space (the acromiohumeral height: the distance or space from the inferior surface of the acromium to the superior surface of the humeral head). The implant is sized to maintain a more anatomic relationship between the glenoid and humeral head and allow rotation of the shoulder without the humeral head pressing on the acromium. Another important sizing consideration is restoration of the height of the subacromial space (the acromiohumeral height mentioned above). The thickness of the implant is determined from known anatomic parameters in the general population (see Table 1, for example) as long as the total thickness of the implant (whether modular or integral) restores or increases the height of the subacromial space. The standard convention is that this height of the subacromial space is a minimum of 7 mm on an AP XRay of the normal shoulder. In an embodiment, the baseplate thickness could be for example a standard 3-4 mm. In such an embodiment, the spacer inserts could have different thicknesses, for example, thicknesses of about 4 mm, about 6 mm, or about 8 mm thickness. The thickness of the spacer will contribute to correcting superior migration of the humeral head and restoring the normal relationship between humeral head and glenoid.

In an embodiment, the implant is of a thickness that allows the restoration of the acromiohumeral height of the shoulder of the subject to the acromiohumeral height of a control shoulder, when implanted in the subject. In an embodiment, the implant is of a thickness that increases the acromiohumeral height of the shoulder of the subject as compared to a control shoulder, when implanted in the subject. The control shoulder may be an uninjured shoulder of the subject or an average of a population representative of the subject.

The baseplate could be of various sizes or alternately be one or two sizes only (eg. small and large) and allow for a minimum posterior fixation. In this instance with only one or two baseplate sizes, the spacer could be modular in a number of sizes but still allow for fixation to the 1 or 2 standard baseplates.

Sizing of the implant could be in a number of ways that would be known to a person of skill in the art. For example, measurements may be obtained directly from a preoperative X-Ray. Alternatively, templates may be used on a preoperative X-Ray to determine implant size. Software programs that 'template' from digital X-rays are known to a person of skill. Additionally, intraoperative measurements could be obtained. Preoperative X-ray templating and intraoperative measurements could be combined to determine the 'best fit' for a particular patient. If, in a particular patient, the X-ray measurements were inadequate, it would be possible to measure/template from the opposite "normal" shoulder or estimate from intraoperative measurements. Templates may be available for tentative selection of the implant based on preoperative radiographs and 'trial' implants would be available for intraoperative determination of the appropriate implant.

FIG. 4A, FIG. 4B and FIG. 4C show an embodiment of a shoulder implant 1 wherein baseplate 25 comprises a biological fixation means 29 which is positioned in a posterior end portion and to abut the overlying acromium. The biological fixation means allows for bone ingrowth between the baseplate and the overlying acromium. In this embodiment, spacer 26 is a poly-articulating spacer and is coupled to a metal baseplate 25. The biological fixation means 29 can be a fixation member and can be composed of, but not limited to, a metallic mesh. In an alternative embodiment, the biological fixation means may comprise an altered surface or a coated surface. The biological fixation means may include a hydroxyapatite coating. In some embodiments a portion of the biological fixation member may comprise a portion of the baseplate, preferably a posterior portion. In an example, portion of the baseplate may be coated with hydroxyapatite. Alternatively, the entire posterior surface of the baseplate may be coated with a suitable material, such as, for example, hydroxyapatite. In another example, a portion, or the entirety of the posterior surface of the baseplate may have a textured surface forming an altered surface, thereby allowing for the ingrowth of bone between the baseplate and the acromium. The biological fixation means allows for bony ingrowth, also known to the person of skill in the art as biological fixation. Biologic fixation allows the implant to remain stably implanted in a subject even if the screws or pins were to loosen or break.

Figure 4:
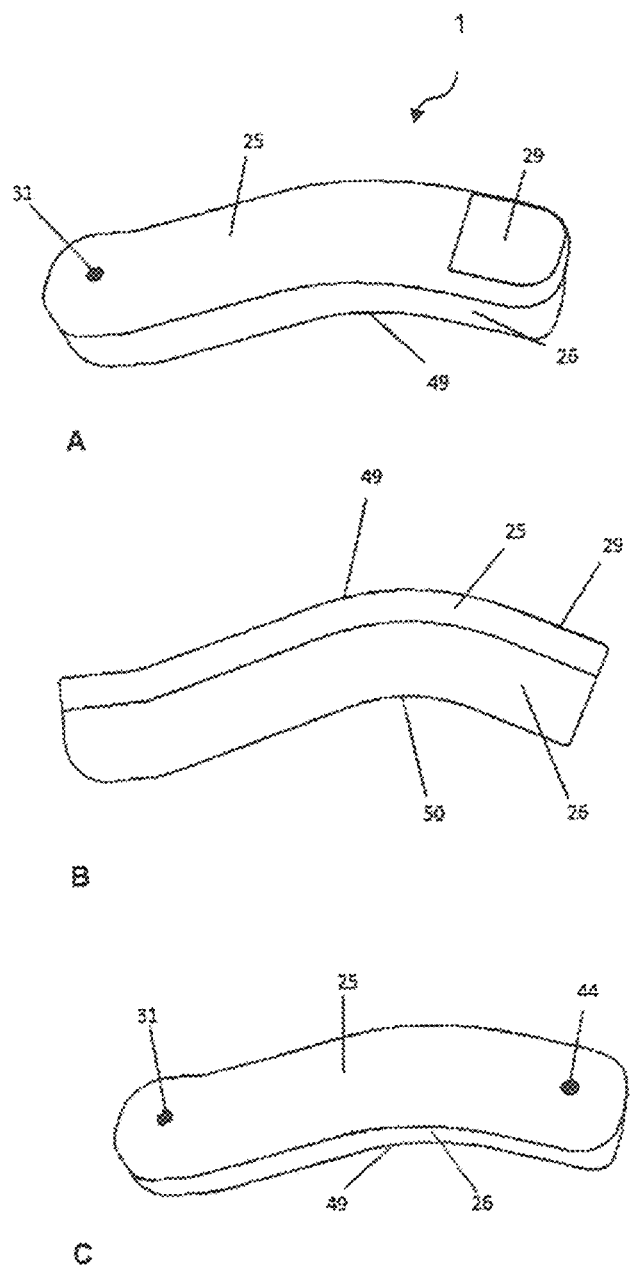
FIG. 4A is a trimetric view of an embodiment of a shoulder implant in accordance with the present disclosure.
FIG. 4B is front view of the embodiment shown in FIG. 4A.
FIG. 4C is trimetric view of the embodiment shown in FIG. 4A, showing the coracoid and acromium screw fixation.

In the embodiment shown in FIG. 4, two apertures (or boreholes) 31, 44 are defined in the baseplate 25 for receiving a mounting member for securing the baseplate to a bone or prosthetic bone. The baseplate 25 has a posterior borehole 44 to allow for screw or pin fixation through the dorsal scapular spine. The shoulder implant 1 follows the contour of the coracoacromial arch on its dorsal surface 49 and the contour of the acromiohumeral arch on its inferior surface 50.

Figure 5:
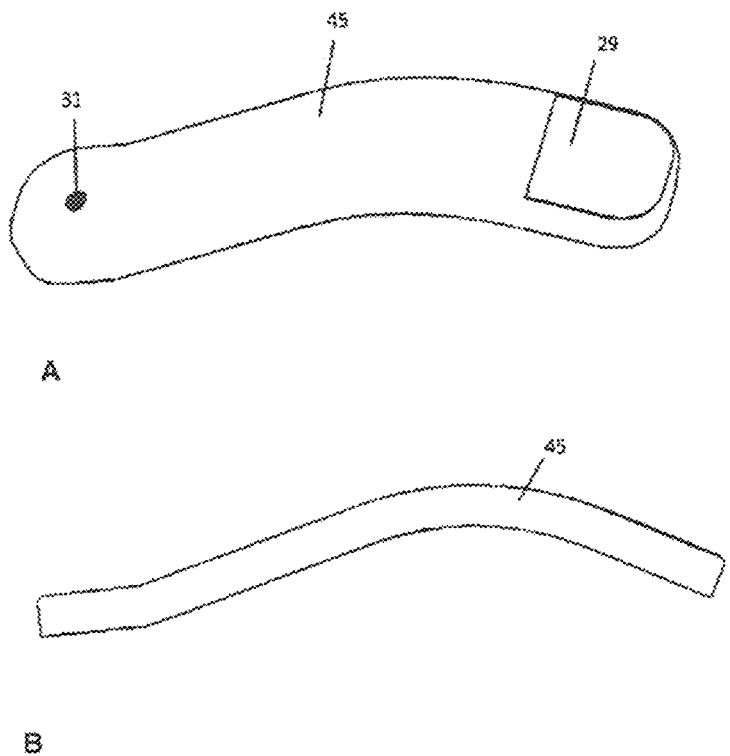
FIG. 5A is a trimetric view of a shoulder implant in accordance with one embodiment disclosed herein, wherein the implant is made of metal.
FIG. 5B is a front view of the embodiment shown in FIG. 5A.

In the embodiment shown in FIG. 5A and FIG. 5B the shoulder implant 45 is unitary in construction. The baseplate and the spacer are made as a single unit shoulder implant 45. As previously described the integral shoulder implant may be made of any biocompatible metal and such materials would be known to a person of skill in the art. The implant in this embodiment defines two apertures each for receiving a mounting member for fixation to a bone. A posterior hole (not shown) is provided to receive a screw for fixation from dorsum or scapular spine to implant. An anterior aperture is shown at 31 for fixation along with a mounting member (not shown) to a coracoid. The shoulder implant 45 has a biological fixation member in the form of a metallic mesh 29 for bone fixation 29.

FIGS. 6A-6D, 7A, 7B and 8A-8C depict embodiments of the shoulder implant wherein the baseplate 25 and the spacer 26 are modular and comprise a retaining means for coupling the baseplate 25 with the spacer 26. The term retaining means is meant to encompass any means of securing the baseplate 25 to the spacer 26. Examples of retaining means include, but are not limited to dovetail-snap-fits, threaded anchors mediating threaded engagement, and any other suitable means including glue or other adhesive. A person of skill in the art would understand the number and positioning of the retaining means required to couple the spacer to the baseplate.

Figure 6:
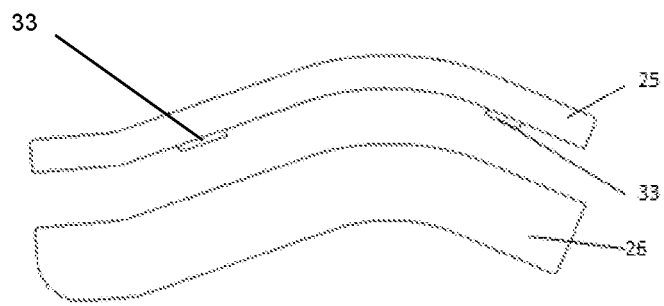
FIG. 6A is an exploded view of an embodiment of an implant in accordance with the present disclosure in which a dovetail snap-fit construct is provided to secure the spacer to the baseplate.
FIG. 6B is an exploded isometric view of the embodiment shown in FIG. 6A.
FIG. 6C is a front view of the embodiment shown in FIG. 6A.
FIG. 6D is a cross section of the of the embodiment shown in FIG. 6A showing the engagement of the male dovetail snap-fit elements with the female dovetail snap-fit elements.
Figure 6:
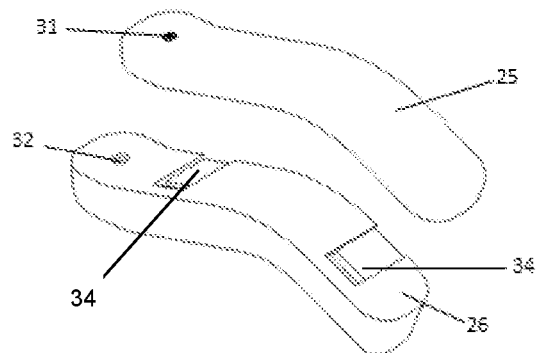
Figure 6:
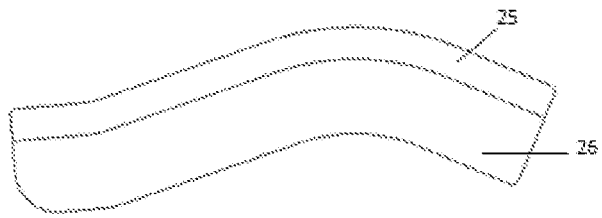
Figure 6:
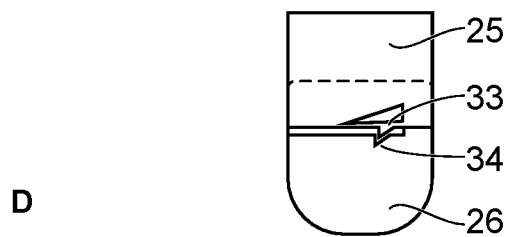

In the embodiment shown in FIGS. 6A, 6B and 6C the baseplate is coupled to the spacer using complementary mating dovetail snap-fit elements. In FIG. 6A it can be seen that the baseplate 25 has a pair of male dovetail-snap-fit elements 33 on the surface of the baseplate that engages the spacer 26 (i.e. the surface opposite the dorsal surface). In FIG. 6B it can be seen that the spacer 26 has a pair of female dovetail-snap-fit elements 34 on the surface for engaging the baseplate 25. The spacer 26 is secured to the baseplate 25 by sliding the female dovetail-snap-fit elements 34 on the spacer onto the male dovetail-snap-fit elements 33 on the baseplate 25. The assembled implant comprising the spacer 26 mounted to the baseplate 25 can be seen in FIG. 6C. It can be seen in FIG. 6D, the male dovetail-snap-fit element 33 will depress into a recessed space and then click into place upon correct alignment with female dovetail-snap-fit element 34. A person of skill in the art would understand that any number of dove-tail snap-fits may be provided such that the spacer 26 is securely retained on the baseplate 25. By securely retained it is meant that the spacer will remain fixed in position with respect to the baseplate when the implant is implanted in a subject. In this embodiment, the spacer 26 has a recess 32 sized and shaped for receiving the end of the fixation member used to secure the baseplate 25 to a bone of a subject or a prosthetic implanted in a subject. The position of aperture 31 and recess 32 are shown in FIG. 6B.

Figure 7:
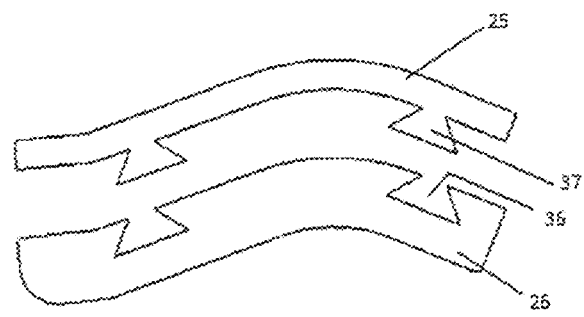
FIG. 7A is an exploded front view of an alternate embodiment of an implant in accordance with the present disclosure in which a dovetail snap-fit element construct is provided to secure the spacer to the baseplate.
FIG. 7B is a right front view of the embodiment shown in FIG. 7A.
Figure 7:
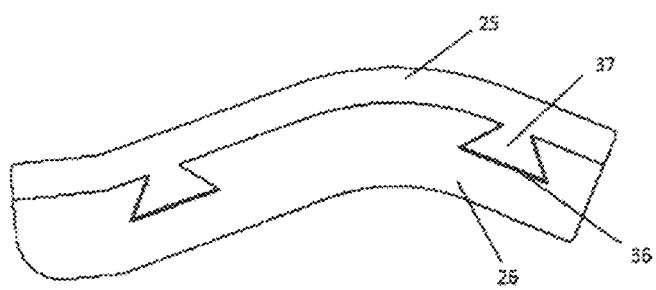

In the embodiment shown in FIGS. 7A and 7B, female dovetail-snap-fit elements 36 are provide on the spacer 26 and male dovetail-snap-fit elements 37 are provided on the baseplate 25. As shown in FIG. 7B, the spacer 26 is secured to baseplate 25 by sliding the female dovetail snap-fit elements 36 on the spacer 26 into the male dovetail-snap-fit elements 37 on the baseplate 25.

Figure 8:
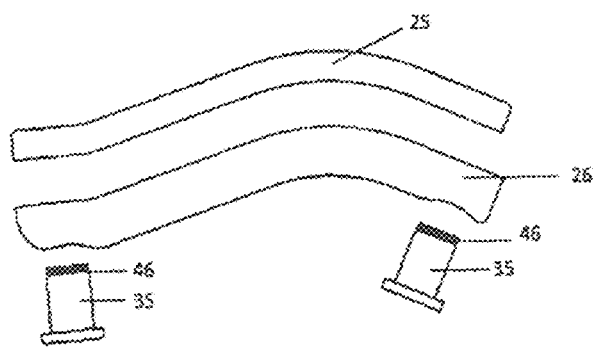
FIG. 8A is an exploded front view of an embodiment of an implant in accordance with the present disclosure in which a threaded anchor is provided to secure the spacer to the baseplate.
FIG. 8B is a front view of the embodiment shown in FIG. 8A.
FIG. 8C is a cross section of the of the embodiment shown in FIG. 8A showing the engagement of the threaded anchor with the mating grooves in the baseplate.
Figure 8:
Figure 8:
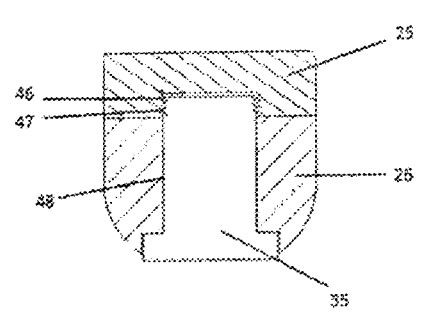
Figure 9:
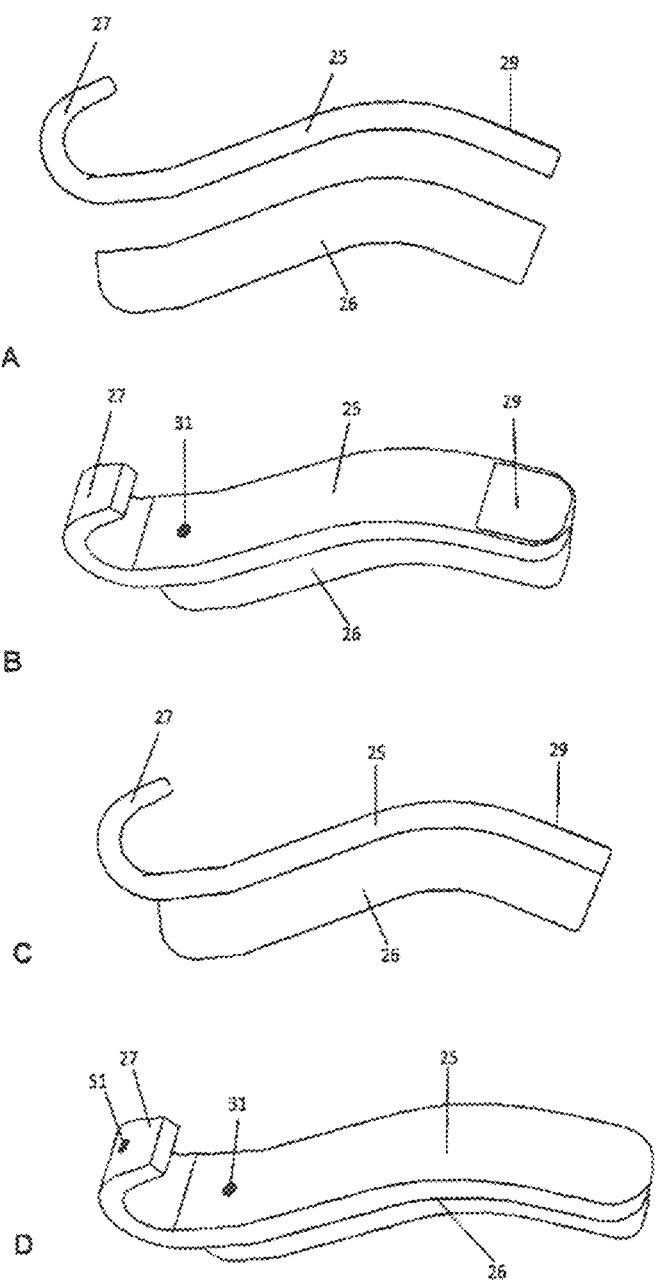
FIG. 9A is an exploded front view of an embodiment of an implant in accordance with the present disclosure having an anterior stabilizing member extending from an anterior end of the implant.
FIG. 9B is a trimetric view of the embodiment shown in FIG. 9A.
FIG. 9C is a front view of the embodiment shown in FIG. 9A.
FIG. 9D is a trimetric view of an embodiment of an implant in accordance with the present disclosure showing a hole in the anterior stabilizing member for receiving a pin or screw for fixation to the coracoid of the subject.

In the embodiment shown in FIGS. 8A, 8B and 8C the spacer 26 is secured to the baseplate 25 by a threaded anchor 35 having mating threads 46. FIG. 8A is an exploded view of the implant showing the spacer 26, the baseplate 25, and a threaded anchor 35 at the anterior and posterior ends of the implant. Each threaded anchor having mating threads 46. FIG. 8B shows the spacer 26 securely coupled to the baseplate 25. As can be seen in FIG. 8C, the threaded anchor 35 may travel superiorly through an aperture 48 defined in the spacer 26 to engage a corresponding aperture 47 defined in the baseplate 25. Aperture 47 does not pass all the way through the baseplate and comprises corresponding mating grooves which engage the mating threads 46 of the threaded anchor 35. In alternate embodiments (not shown), the threaded anchor 35 may instead travel from the dorsal surface of baseplate 25, through baseplate 25 and into the spacer 26.

FIG. 9A-9D and FIG. 10A-10C show different embodiments of a shoulder implant each having a stabilization member for further stabilizing the implant to a bone within the joint. In the embodiment shown in FIG. 9 the stabilization member is an anterior stabilization member 27, while the embodiment shown in FIG. 10 is a posterior stabilization member 38. The embodiments comprising a stabilization means may be made as a single unit or may be one or more pieces that are stably connected to the baseplate by any suitable means as previously described. The implant may comprise both an anterior and a posterior stabilization member.

FIG. 9A is an exploded front view of an embodiment of an implant having an anterior stabilizing member extending from an anterior end of the implant. FIG. 9B is a trimetic view of the embodiment. FIG. 9C is a front view of the embodiment. FIG. 9D is a trimetic view of an embodiment showing a hole in the anterior stabilizing member for receiving a pin or screw for fixation to the coracoid of the subject.

In the embodiment shown in FIG. 9A, FIG. 9B, FIG. 9C and FIG. 9D, the baseplate 25 has a coracoid extension 27 extending anteriorly from the baseplate 25 at the anterior end coracoid end of the baseplate. The coracoid extension 27 is sized and shaped to engage a coracoid process of a subject and is for securing the baseplate to the coracoid of the subject providing additional stabilization. A mounting member (not shown) in the form of for example a pin or screw, may be inserted through aperture 31 defined in the baseplate 25 further securing the implant to the coracoid. A posterior aperture is also provided (not shown) in the baseplate for posterior fixation of the implant. The coracoid extension 27 may be of a hooked configuration of a shape the mimics the contour of the coracoid which is sufficient to provide stabilization. However, as shown in FIG. 9D the baseplate 25 may comprise a further borehole 51 at the end of the coracoid extension 27 to receive a pin or screw for additional fixation of the baseplate 25 to the coracoid. As described in previous embodiments, the baseplate 25 may include a biological fixation means 29. The coracoid extension may comprise a biological fixation means in addition to a posterior biological fixation means 29. For example, the stabilization member 27 may be coated with hydroxyapatite or may also comprise a biological fixation member such as a metallic mesh, for biologic fixation to the coracoid process (not shown).

In the embodiment shown in FIG. 10A, FIG. 10B and FIG. 10C, the baseplate 25 has a posterior, scapular spine extension 38 extending posteriorly from the baseplate 25 at the posterior end for stabilizing the implant to a scapular spine of a subject. FIG. 10A is an exploded front view of an embodiment of an implant having a posterior stabilizing member extending from a posterior end of the implant that may be secured to the scapular spine of the subject and showing the positioning of the implant in a shoulder. FIG. 10B is an isometric view. FIG. 10C is a right view of the embodiment showing posterior/acromium screw fixation points. The scapular extension 38 extends posteriorly and is secured with a mounting member (not shown), i.e. a fixation screw or pin through one or more apertures 39 and into the scapular spine. A screw or pin (mounting member) 43 may be passed through the dorsum of the scapular spine to further secure the metal baseplate 25 to the acromium. The scapular spine extension 38 of the shoulder implant allows for additional screw fixation to the scapular spine. The scapular spine extension 38 will have a curvilinear shape to accommodate the shape of the scapular spine and extend from the posterior aspect of the baseplate onto the posterosuperior scapular spine and extend medially along the spine inferior to the dorsal subcutaneous surface or alternatively, travel medially along the dorsal subcutaneous surface of the spine. The length of the scapular extension 38 will vary depending on the size and anatomy of the subject. The size of the scapular extension that extends onto the scapular spine could range from 2 to 6 screw holes.

As with the earlier described embodiments, the screw(s) or pin can be coated with a material to allow for biologic fixation to host bone. Stable biologic fixation of the posterior aspect of the device may also be enhanced by the altered surface (not shown) of the posterior baseplate. In a further embodiment, the scapular spine extension 38 may be present an optionally includes an anterior extension to the coracoid for further stabilization.

In embodiments having an anterior or posterior attachment member it is not required for the spacer to extend the entire length of the baseplate. Regardless of whether an additional stabilization member is provided, in most embodiments the spacer will extend from the anterior to the posterior edge of the acromium. In some embodiments, in particular for embodiments for use in in subjects with anterosuperior escape of the humeral head, it is important for the spacer to extend to the anterior (coracoid) limb. In an embodiment, wherein the implant is a unitary construction, the stabilization may extend from the posterior and/or anterior end of the implant.

Figure 11:
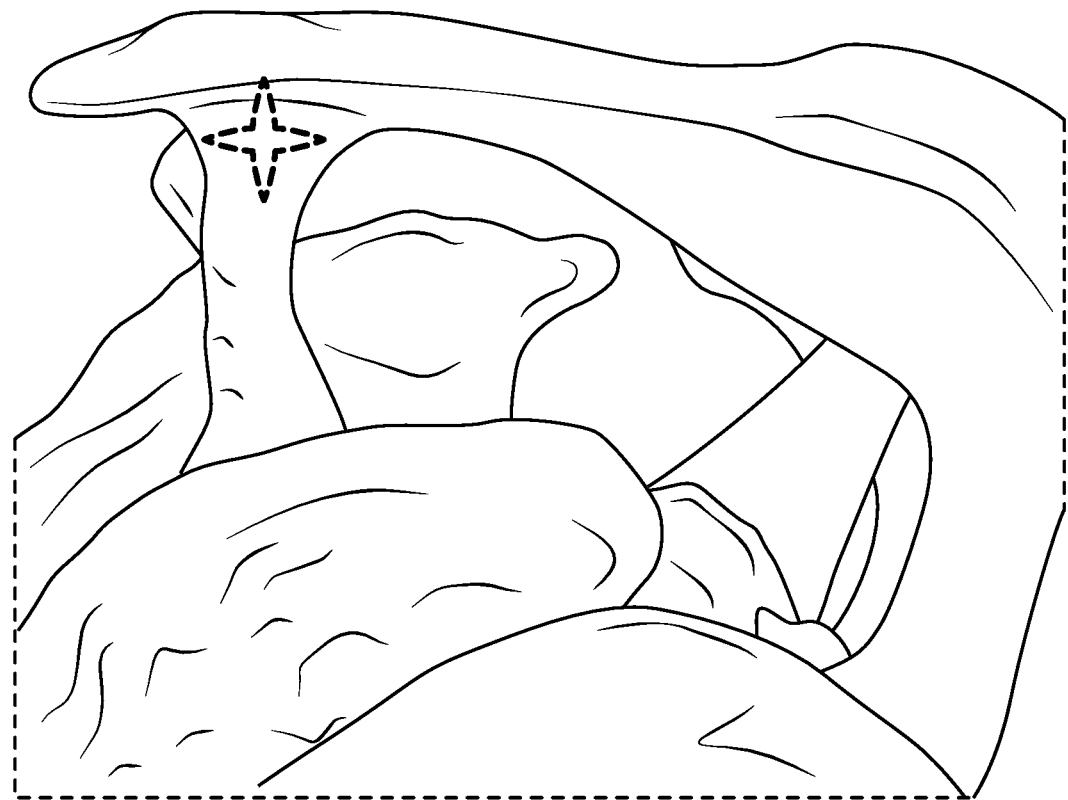
FIG. 11 is a side view of a scapula showing the fixation point for an embodiment of an implant on the spinous process.

As seen in FIG. 11, posterior fixation of the device may take place at the spinous process of the scapula. The area of the scapula around the spinous process is relatively subcutaneous and does not require extensive surgery for exposure. The spinous process has 'thicker' cortical bone than the thinner bone of the acromium. The 'star' in FIG. 11 localizes placement of the fixation screw or pin placed through the spinous process. In accordance with the embodiment shown, accurate placement of the screw or pin can be facilitated by an 'outrigger' drill guide temporarily positioned on the baseplate (not shown). The spinous process provides stronger fixation of the device with an orthopaedic screw or pin than can be achieved solely by the thinner acromial bone. Supplemental screw(s) can be placed through the posterior extension 38 (FIG. 10) of the implant into the scapular spine.

Figure 12:
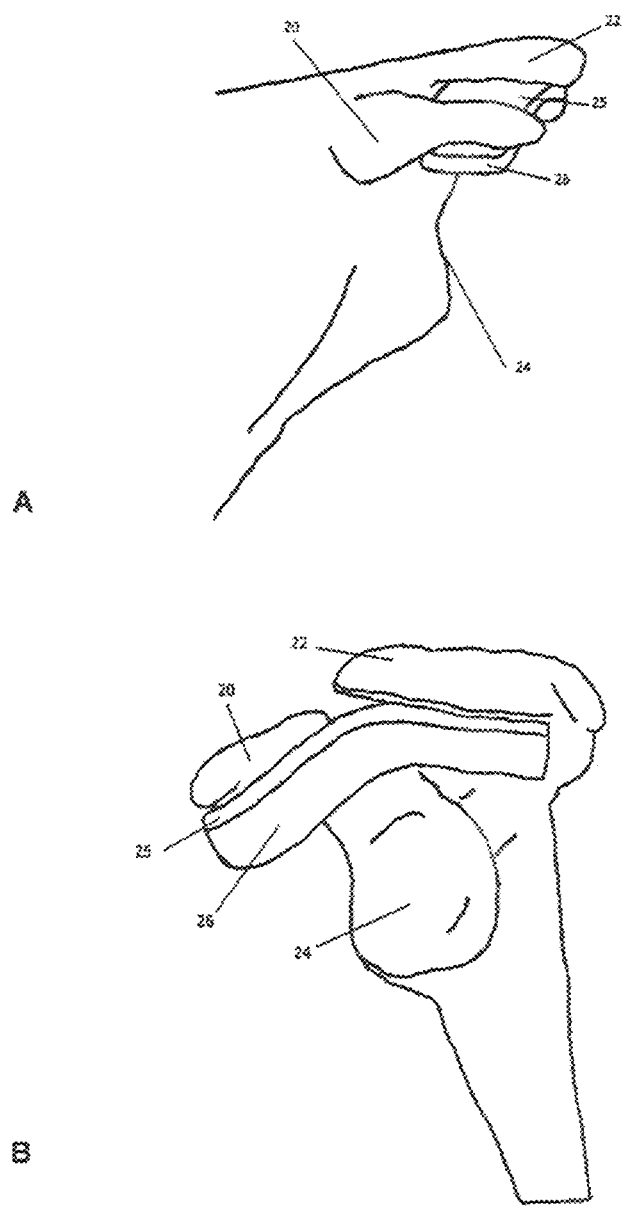
FIG. 12A shows an anterior view of the placement of an embodiment of a shoulder implant in accordance with the present disclosure in a shoulder of a subject.
FIG. 12B shows a lateral view of the placement of a shoulder implant in accordance with the present disclosure in a shoulder of a subject.

FIG. 12A shows an anterior view of the positioning of a shoulder implant in a shoulder joint of a subject. FIG. 12B shows a lateral view of the placement of a shoulder implant in a shoulder of a subject. Shoulder implant comprises baseplate 25 coupled to spacer 26 is positioned in the shoulder joint below the coracoid process 20 and the acromium 22 to restore the CA arch of the shoulder. Positioning of the implant with respect to the glenoid 24 can also be seen. Normal glenohumeral joint anatomy is restored. The implant restores the normal acromiohumeral arch and restores the height of the subacromial space such that abnormal humeral head migration is corrected a more normal glenoid-humeral head articulation is restored. The shoulder implant articulates within the shoulder joint and helps to maintain the normal relationship between a native intact humeral head (or a prosthetic humeral head) and a glenoid.

The implanted shoulder implant provides a number of benefits. The disclosed implant is designed to restore a more normal coracoacromial arch and acromiohumeral arch, which leads to improved glenohumeral joint anatomy. This improved anatomy can lead to relief of shoulder pain, improved function and may delay or minimize the onset of cuff tear arthropathy. The shoulder implant is designed for insertion into the shoulder so as not to interfere with the integrity of the glenoid or the humeral head. This preservation of the bone 'stock' (anatomic integrity) of the glenoid and humerus is important for the success of future surgery, such as a reverse shoulder replacement, which may become a surgical consideration in the older patient.

Figure 13:
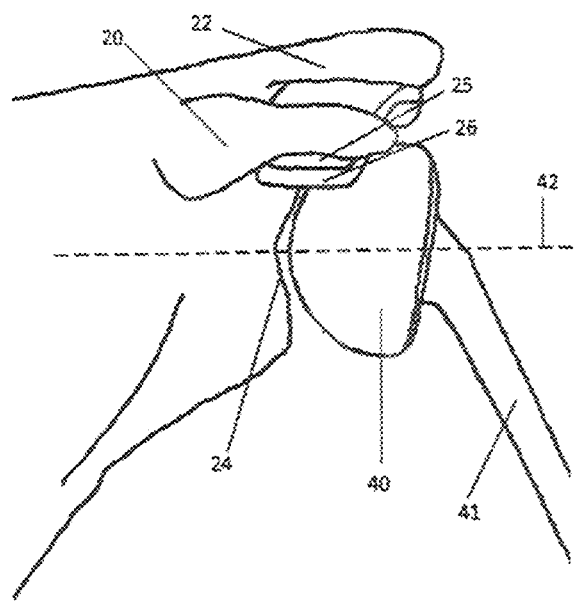
FIG. 13 shows an anterior view of an embodiment of the shoulder implant in accordance with the present disclosure in situ a prosthetic humeral head.

FIG. 13 shows an anterior view of an embodiment of the shoulder implant for use with a humeral implant. The shoulder implant can also be used with any of the commonly used humeral head components such as a humeral head implant composed of a prosthetic humeral head 40 and humeral stem 41 or a resurfacing humeral head component. The shoulder implant keeps the natural glenoid 24—humeral 40 alignment (shown as dashed line 42). Shoulder implant comprises baseplate 25 coupled to spacer 26 is positioned in the shoulder joint below the coracoid process 20 and the acromium 22 to restore the CA arch of the shoulder.

Also disclosed herein is a method of stabilizing a shoulder using the shoulder implants disclosed herein. When the implant is modular the method would include a first step of fixing the baseplate to a bone of a subject. Preferably, the fixation is posterior fixation. The spacer is then coupled to the baseplate. When the implant is integral, the method includes a single step of fixing the implant to a coracoid process or scapular spine, preferably a posterior portion of the scapular spine. In an embodiment, the baseplate or implant contacts the posterior acromium to allow for fixation of the implant and biologic ingrowth. This allows fixation of the implant without damaging the glenoid, humeral head or acromium.

The shoulder implants disclosed herein would typically be utilized in the shoulder patient with a massive cuff tear and intact glenohumeral joint but could also be used in conjunction with a 'partial' (hemiarthroplasty with humeral head implant) shoulder replacement or 'total' (glenoid and humeral head implants) shoulder replacement. Surgical technique would entail a limited open approach to the coracoid process at the anterior aspect of the shoulder and a second limited open approach to the spinous process and acromium at the posterior aspect of the shoulder. Alternately, a deltopectoral approach could be utilized for exposure of the coracoid process and implant insertion. Open surgery for insertion of the implant could be undertaken in conjunction with minimally 'invasive' arthroscopic surgery. For example, arthroscopic surgery could be utilized to debride remnants of the rotator cuff or to prepare the posteroinferior acromium for bone integration to the implant. Insertion of this device would not require a formal surgical approach with dislocation of the glenohumeral joint. Surgical procedures for implanting the shoulder implant would be known to a person of skill in the art.

In the preceding description, for purposes of explanation, numerous details are set forth in order to provide a better understanding of the embodiments. However, it will be apparent to one skilled in the art that these specific details are not required. The above-described embodiments are intended to be examples only. Alterations, modifications and variations can be effected to the particular embodiments by those of skill in the art without departing from the scope, which is defined solely by the claims appended hereto. The references recited herein are incorporated by reference in their entirety.

The invention claimed is:

1. A shoulder implant for implanting into a subject, the shoulder implant comprising:
   a body, the body comprising:
   a shoulder implant dorsal surface substantially shaped as a coracoacromial arch of a reference shoulder, the dorsal surface for engaging at least an acromium posterior portion of an acromium of the subject when the shoulder implant is implanted in the subject;
   a shoulder implant inferior surface substantially shaped as an acromiohumeral arch of the reference shoulder, the shoulder implant dorsal surface being opposite the shoulder implant inferior surface; and
   a stabilization member coupled to the body for stabilizing the shoulder implant to a bone when implanted in the subject, wherein the stabilization member is a scapular spine extension that extends posteriorly from a posterior end of the body and is shaped to allow fixation to a scapular spine of the subject.

2. The shoulder implant according to claim 1, wherein the shoulder implant dorsal surface is sized and shaped to be coextensive with an acromium inferior surface of the acromium of the subject.

3. The shoulder implant according to claim 1, wherein the shoulder implant is of a thickness that allows the restoration of the acromiohumeral height of the shoulder of the subject to an acromiohumeral height of a control shoulder, when implanted in the subject.

4. The shoulder implant according to claim 1, wherein the implant is of a thickness that maintains the acromiohumeral height of the shoulder of the subject when implanted in the subject.

5. The shoulder implant according to claim 1, wherein the shoulder implant comprises:
   a spacer comprising the shoulder implant inferior surface and further comprising a second surface opposite the shoulder implant inferior surface;
   a baseplate comprising the shoulder implant dorsal surface and further comprising a second surface opposite the shoulder implant dorsal surface,
   the second surface of the spacer being coupled to the second surface of the baseplate.

6. The shoulder implant according to claim 5, wherein the spacer comprises at least one coupling feature and the baseplate comprises at least one complementary coupling feature for engaging with the at least one coupling feature on the spacer for coupling the baseplate to the spacer.

7. The shoulder implant according to claim 5, wherein the baseplate defines at least one aperture for receiving a mounting member, each aperture to receive a respective mounting member, each mounting member for coupling the shoulder implant to a native or prosthetic bone of the subject.

8. The shoulder implant according to claim 7, wherein the baseplate comprises a baseplate anterior portion and a baseplate posterior portion and wherein at least one of the at least one aperture is defined in the baseplate posterior portion for receiving a respective mounting member for coupling the shoulder implant to an acromium of the subject.

9. The shoulder implant according to claim 8, wherein the baseplate defines two apertures, one of which is defined in the baseplate anterior portion for receiving a respective mounting member for coupling the shoulder implant to a coracoid process of the subject.

10. The shoulder implant according to claim 5, wherein the spacer extends along a length of the baseplate.

11. The shoulder implant according to claim 1, wherein the shoulder implant dorsal surface and the shoulder implant inferior surface are substantially the same shape.

12. The shoulder implant according to claim 5, wherein the spacer is an articulating spacer.

13. The shoulder implant of claim 1, further comprising an anterior stabilization member coupled to the body, wherein the anterior stabilization member is a coracoid extension extending anteriorly from an anterior end of the body and shaped to engage a coracoid process of the subject, for securing the shoulder implant to the coracoid process.

14. The shoulder implant according to claim 1, wherein the shoulder implant further comprises a biological fixation member for allowing bone ingrowth and biological fixation of the shoulder implant to the bone.

15. The shoulder implant according to claim 5, wherein the baseplate comprises a biological fixation member for allowing bone ingrowth and biological fixation of the shoulder implant to the bone.

16. The shoulder implant according to claim 1, wherein the stabilization member comprises a biological fixation member for allowing bone ingrowth and biological fixation of the implant to the bone.

17. The shoulder implant according to claim 14, wherein the shoulder implant dorsal surface comprises the biological fixation member, and the biological fixation member comprises a portion of the shoulder implant dorsal surface comprises an altered texture relative to a remainder of the shoulder implant dorsal surface.

18. The shoulder implant according to claim 1, wherein the shoulder implant comprises:
   an anterior end portion;
   a posterior end portion adjacent opposite the anterior end portion; and
   a coracoacromial arch portion extending between the anterior end portion and the posterior end portion, wherein the coracoacromial arch portion has an arc radius which substantially corresponds to the arch radius of a humerus.

19. The shoulder implant according to claim 1, wherein the body and the stabilization member are unimodular.

20. The shoulder implant according to claim 1, wherein the body and the stabilization member are made of the same orthopaedic material.

* * * * *